Jan. 9, 1962 A. ASSERETTO Plant Pat. 2,120
ROSE PLANT
Filed Jan. 26, 1960
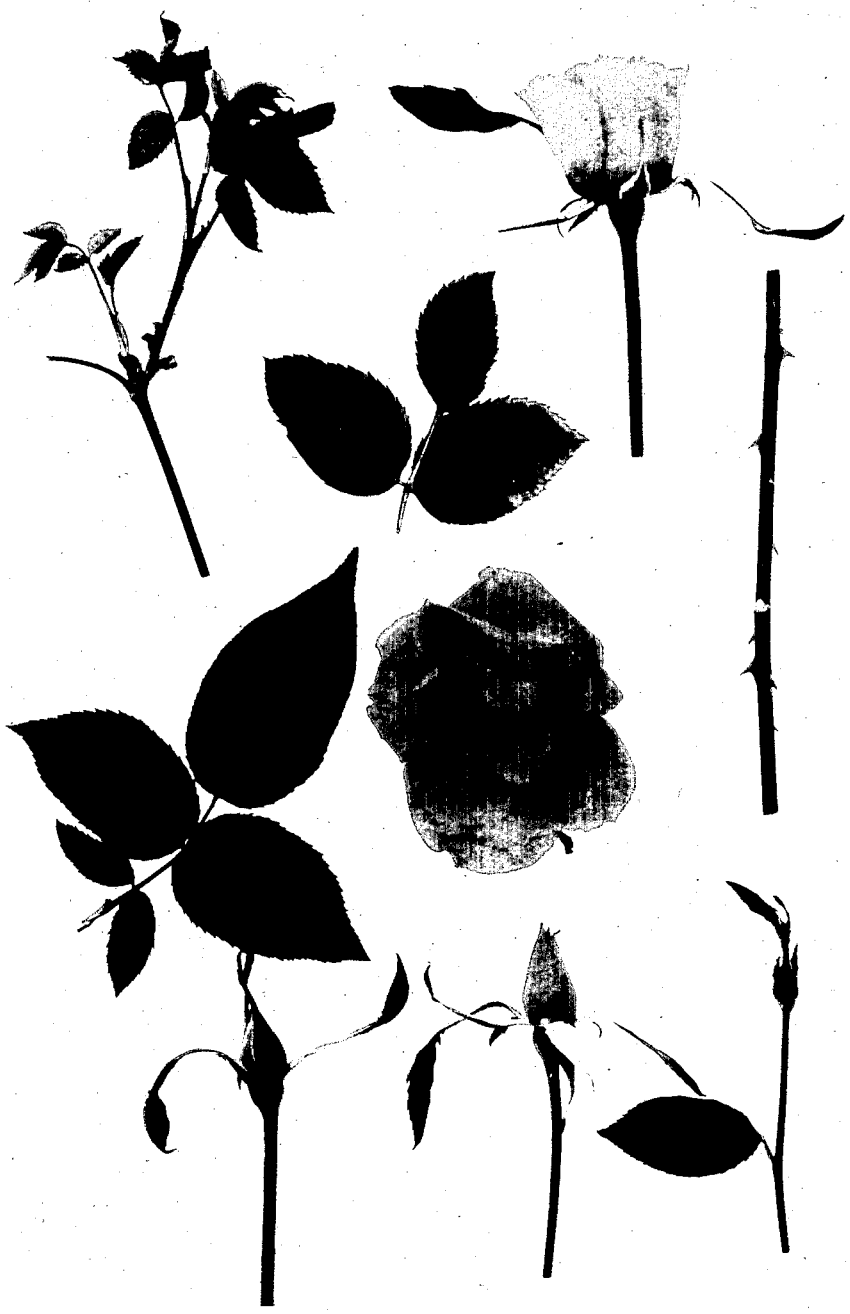
INVENTOR
ANGELO ASSERETTO
By Irvin S. Thompson
ATTY.

United States Patent Office

Plant Pat. 2,120
Patented Jan. 9, 1962

2,120
ROSE PLANT

Angelo Asseretto, Sanremo (Imperia), Italy, assignor to Michel Blanchon, Paris, France Filed Jan. 26, 1960, Ser. No. 4,841
Claims priority, application Italy Jan. 31, 1959
1 Claim. (Cl. 47—61)

The present invention relates to a new and distinct variety of rose plant of the hybrid tea class, which was originated by me by crossing an unnamed rose plant variety designated No. 225 with the variety "Poinsettia" (both unpatented).

The object of this breeding was to produce a new rose variety having a flower color which lies between rose red and cherry red capable of being cultivated on a large scale for the production of cut flowers and for the cultivation of ornamental rose plants both indoors and out-of-doors.

Asexual reproduction of my new variety by budding on rose plants of the variety "Indica Major" (unpatented) at San Remo, Italy, show that the distinguishing features of my new variety come true to form and are established and transmitted through succeeding generations.

The accompanying drawing shows in color typical specimens of the vegetative growth and flowers of my new variety in different stages of development.

The following is a detailed description of my new variety, with color terminology in accordance with the Horticultural Color Chart of Robert F. Wilson, except where general color terms of ordinary dictionary significance are obvious.

Botanical and commercial classification: Hybrid tea.
Parentage: Seedling.
Seed parent: Unnamed variety designated No. 225.
Pollen parent: "Poinsettia."

*Flower*

Habit: Erect, single, sometimes accompanied by a secondary floral bud which is smaller than the main flower, flower axis in line with the axis of the stem.

Peduncle of the flower: Very long, stiff and resistant, erect, length up to 120–150 mm., rectilinear or slightly incurved, carrying fine fleshy prickles which are short and soft and almost in the shape of short hairs. Outer surface: green sage color (Wilson, page 198, shade 61) tinged with a reddish brown color (Wilson, page 185, shades 30–30/1).

Receptacle: Small with reference to the flower, almost conical, but scarcely differentiated.

Closed floral bud:

*Shape.*—Sharply pointed triangular outline, the tip of the bud being capped by leaf-shaped expansions of different lengths which are sometimes longer than the sepal.

*Size.*—Average length of the bud—25–35 mm. Average diameter—20–25 mm.

*Sepals.*—Five in number, large, turned over the receptacle even before the complete opening of the flower. Shape—broad and triangular with an extension at the tip in the shape of leave-shaped appendices of various outlines and sizes, broadening often into a leaf-shaped serrated limb. Size: average length including the leaf-shaped appendix—50–80 mm.; average breadth of the sepal at its base—4–8 mm.; breadth of the sepal in registry with the leaf-shaped appendix varying up to 12–15 mm.

*Color.*—Upper surface—foundation color—lavender green (Wilson, page 196, shades 61–61/1) sometimes with a central longitudinal streak of a color approximating barium yellow (Wilson, page 131, shades 3–3/1).

Half-open floral bud: In the form of a rounded, more or less elongated urn flaring upwardly at the opening of the flower and then of an almost globular shape.

*Size.*—Between medium and large. Average length—45–55 mm. Average diameter—60–70 mm.

*General color of the half-open bud.*—Approximating crimson chrysanthemum (Wilson, page 169, shades 24/1–2–3).

Open Corolla: In the shape of a widely flaring cup facing upwardly with an irregular round or elliptic outline provided with a few apices produced by an outward rolling of the petals. Outer petals fully open and separate from the other petals; inner petals interengaging one another and including a few irregularly formed petals at the center of the corolla. Inner petals, the edges of which are slightly incurved outwardly, the center is concave when the corolla is completely opened.

*Size.*—Diameter upon complete opening—90–120 mm.

*Genral color.*—Between rose red (Wilson, page 158, shade 24) and cherry red (Wilson, page 175, shade 22).

*Petals.*—Between average number and large number 20–40 as an average. Shape—fully open limb, oval, very rounded, somewhat broader than long, small claws, hardly differentiated. Size: large outer petals—average length, 55–75 mm., breadth, 60–85 mm.; inner petals—length, 45–60 mm., breadth, 45–65 mm. Color: upper surface between rose red (Wilson, page 158, shade 24) and crimson chrysanthemum (Wilson, page 169, shades 24/1–2) with tones and glimmers of Tyre purple (Wilson, page 159, shade 27/1) at the base and center of the petals; lower surface approximating crimson chrysanthemum (Wilson, page 169, shades 24/1–2); claw—color approximating mimosa yellow (Wilson, page 143, shades 2/2–1) over an extent of 6–2 mm. slightly tinged with the red of the limb on its upper surface, same color over a small extent, hardly marked on its lower surface. Surface: upper surface slightly rough and velvety with fine veins; lower surface slightly rough, satin-like, with small veins extending fanwise into the limb. Structure: of an average thickness, resistant.

Reproductive organs: Stamens—medium number, length up to 6–10 mm., shorter than the styles, average 90–130 mm. Filaments—strong, thick, erect, tinged with crimson color, of a varying tone. Anthers—large, biloculated, of an irregular shape, color approximating mimosa yellow (Wilson, page 143, shades 2/1–2). Ovary—almost completely enclosed inside the receptacle. Styles—medium number, free, 40–60 as an average, color approximating uranium green (Wilson, page 63, shades 63/2–3) tinged with red at their apices. Stigma—elongated tubes of a yellowish color.

Fragrance: Perceptible, with a touch of tea.

*Plant*

Growth: Erect, bushy, of an average compactness, vigorous and speedy growth, very floriferous.

Radicular system: Strong, well branched, entering the ground.

Height: Up to 120–160 cm. above ground for plants after two-year grafting on an Indica Major rose plant cultivated in a greenhouse, 100–120 cm. above ground for plants cultivated out-of-doors after five-year grafting on an Indica Major rose plant.

Stem and main branches: Strong, ligneous, with a rough cortex, prickles of an average distribution, length—5–7 mm., breadth—3–6 mm., thickness—1–2 mm., slightly ligneous. Prickles needle-shaped or almost absent, small and short. Main stem—diameter at the location of the grafting—15–25 mm.

Floral stems: Numerous, erect, straight, vertical, thin, jointed so as to form internodes of a length of 40–60 mm., rectilinear or slightly sinuous.

*Cortex.*—Smooth, thin, satin-like, hardly brilliant.

*Color.*—Foundation color—sage green (Wilson, page 198, shade 61), largely tinged and covered with reddish brown (Wilson, page 185, shades 30–30/1).

*Structure.*—Semi-ligneous and rigid.

*Prickles.*—Medium number, rare and short. Shape—triangular, with a very short tip, differentiated and turned downwardly. Size—from small to average; average length—4–6 mm.; average breadth—1–3 mm. Color—approximating pansy purple (Wilson, page 177, shades 28/1–2) with a tip sometimes tinged with a hardly perceptible greenish color. Structure—slightly ligneous, readily removable from the stem. Prickles in the shape of needles absent on the stems and present in average number on the flower carrying peduncles, small and soft, forming almost glandular hairs.

Leaves: Numerous, large with reference to the stem, located on the stems in a dispersed distribution, almost alternating in registry with the nodes.

*Shape.*—Including three, five or seven leaflets located in opposite pairs on the rachis with the addition of a terminal leaflet.

*Size.*—Average length between the beginning of the stem up to the tip of the terminal leaflet—90–130 mm. Average breadth between the tips of opposite leaflets—80–100 mm.

*Leaflets.*—Average size, thin, and broad limb widely open, oval, spear-shaped with an average rounding and finely serrated edges. Size: varying very slightly from one pair to the other and increasing from the bottom of the leaf towards the terminal leaflet; average length—first pair starting from the base—25–45 mm.; second pair—40–55 mm.; third pair—45–55 mm.; terminal leaflet—55–65 mm.; average breadth—first pair starting from the base—20–25 mm.; second pair—25–35 mm.; third pair—30–40 mm.; terminal leaflet—30–40 mm.

*Color.*—Upper surface—approximating parsley green (Wilson, page 193, shades 62–62/1), tinged with intense ivy green (Wilson, page 200, shades 60/2–3); lower surface—foundation color—willow green (Wilson, page 199, shades 62–62/1) with local spots in the limb and along the edges of the serrations of a color approximating reddish brown (Wilson, page 185, shades 30–30/1). Said color, of a considerable intensity, invades all the tissues of the stems and leaves in the young plant.

*Surface.*—Upper surface—smooth, without any hairs, of an average brilliancy, with fine pennate and branched vein system extending over the limb and with leaf-shaped elements slightly in relief in the intervals between the veins; lower surface—opaque, slightly velvety, with fine veins in relief, pennated, and branched.

*Structure.*—Of an average thickness, semi-herbaceous, resistant.

*Rachis.*—Average length, rectilinear or slightly sinuous, subdivided into uniform intervals by the leaflets inserted thereon. Transverse cross-section almost in the shape of a gutter, with a well-defined longitudinal groove and provided with fine glandular hairs along its edges, in the upper surface. Small soft prickles with sharp tips folded downwardly, as an average—3–6 on the lower surface.

*Stipules.*—Small, along the rachis up to about one half of the interval between the stem and the first pair of leaflets, narrow, with thin ears, divergent with reference to the rachis. Average length—12–20 mm. including the ears of 4–6 mm. Average breadth—2–4 mm.

Resistance of the flowers to inclement weather: Excellent.

Resistance of the flowers to transportation: Excellent.

Behaviour of the cut flowers: Excellent—10–12 days for flowers gathered out-of-doors at San Remo, Italy, in the month of December and kept at room temperature.

What I claim is:

A new and distinct variety of rose plant of the hybrid tea class, substantially as herein shown and described, characterized particularly as to novelty by its large long-lasting flower of a color between rose-red and cherry-red, elongated floral peduncles, generally thin and erect floral stems, distinctive green foliage and vigorous growth.

No references cited.